(12) United States Patent
Ghigo et al.

(10) Patent No.: US 8,071,368 B2
(45) Date of Patent: Dec. 6, 2011

(54) METHODS FOR PROMOTING GROWTH AND SURVIVAL OF INSULIN-SECRETING CELLS

(75) Inventors: Ezio Ghigo, Turin (IT); Aart Jan Van Der Lely, Bergschenhoek (NL)

(73) Assignee: Alizé Pharma SAS, Écully (FR)

( * ) Notice: Subject to any disclaimer, the term of this patent is extended or adjusted under 35 U.S.C. 154(b) by 41 days.

(21) Appl. No.: 12/604,909

(22) Filed: Oct. 23, 2009

(65) Prior Publication Data

US 2010/0196330 A1 Aug. 5, 2010

Related U.S. Application Data

(60) Division of application No. 11/756,456, filed on May 31, 2007, now Pat. No. 7,666,833, which is a continuation-in-part of application No. 10/499,376, filed as application No. PCT/CA02/01964 on Dec. 18, 2002, now Pat. No. 7,485,620.

(30) Foreign Application Priority Data

Dec. 18, 2001 (CA) .................................... 2365704

(51) Int. Cl.
*C12N 5/00* (2006.01)
*A61K 35/39* (2006.01)
*A61K 38/00* (2006.01)

(52) U.S. Cl. ......................... 435/325; 424/520; 530/300

(58) Field of Classification Search ........................ None
See application file for complete search history.

(56) References Cited

U.S. PATENT DOCUMENTS 7,825,090 B2 11/2010 Ghigo et al.

FOREIGN PATENT DOCUMENTS

| | | |
|---|---|---|
| CA | 2470235 A1 | 6/2003 |
| CA | 2471879 A1 | 11/2003 |
| CA | 2543507 | 5/2005 |
| WO | 01/56592 | 8/2001 |
| WO | 01/87335 | 11/2001 |
| WO | 01/92292 A2 | 12/2001 |
| WO | 02/060472 A1 | 8/2002 |
| WO | 03/051389 | 6/2003 |
| WO | WO 2005/039624 A1 | 5/2005 |
| WO | 2006/045319 | 5/2006 |
| WO | WO 2007/126792 A1 | 11/2007 |
| WO | WO 2008/145749 A1 | 12/2008 |

OTHER PUBLICATIONS

Baldanzi et al., Ghrelin and des-acyl ghrelin inhibit cell death in cardiomyocytes and endothelial cells through ERK1/2 and PI 3-kinase/AKT, J. Cell Biol., 159:1029-1037 (2002).

Li et al., Cardioprotective effects of ghrelin and des-ghrelin on myocardial injury induced by isoproterenol in rats, Acta Pharmacologia Sinica, 27:527-535 (2006).
Office Action issued on Oct. 1, 2010 in connection with U.S. Appl. No. 12/130,615, 8 pp.
Office Action issued on Apr. 29, 2010 in connection with U.S. Appl. No. 12/130,615, 11 pp.
Office Action issued on Oct. 16, 2009 in connection with U.S. Appl. No. 12/130,615, 18 pp.
International Search Report mailed on Jan. 25, 2010 in connection with International Patent Application PCT/EP2009/057263 (WO 2009/150214 A3).
Granata, et al., Acylated and Unacylated Ghrelin Promote Proliferaion and Inhibit Apoptosis of Pancreatic beta Cells and Human Islets: Involvement of 3', 5'—Cyclic Adenosine Moriophosphate/Protein Kinase A. Extracellular Signal-Regulated kinase 1/2, and Phosphatidyl Inositol 3-Kinase/Akt Signaling, Endocrinology, vol. 148, No. 2, pp. 512-529, 2007.
Granata, et al., Acylated and unacylated ghrelin promote proliferation and inhibit serum stravation- and cytokine-induced apoptosis of pancreatic beta cells through cAMP/PKA, ERK 1/2 and PI3K/Akt, Abstract and poster presented at Meeting of the Endocrine Society, Boston, from Jun. 24, 2006.
Prodam, et al., Unacylated Ghrelin (UAG) Enhances the Early Insulin Response to Meal, Improves Glucose Metabolism and Decreases Free Fatty Acids Levels in Health Volunteers, Abstract and poster presented at European Congress of Endocrinology, Budapest, from Apr. 28, 2007 to May 2, 2007.
Cassoni, et al., "Identification, Characterization, and Biological Activity of Specific Receptors for Natural (Ghrelin) and Synthetic Growth Hormone Secretagogues and Analogs in Human Breast Carcinomas and Cell Lines," The Journal of Clinical Endocrinology & Metabolism, vol. 86. No. 4, pp. 1738-1744, 2001.
Toshinai, et al., "Upregulation of Ghrelin Expression in the Stomach upon Fasting, Insulin-Induced Hypoglycemia, and Leptin Administration," Biochemical and Biophysical Research Communications, vol. 281, pp. 1220-1225, 2001.
Mickle and Cutting, "Genotype-Phenotype Relationships in Cystic Fibrosis," Med. Clin. North Am., 2000, vol. 84(3), p. 597-607.
Adelhorst, et al., "Structure-Activity Studies of Glucagon-like Peptide-1," J. Biol. Chem. 269: 6275-6278, 1994.
Marzullo, et al., "The Relationship between Active Ghrelin Levels and Human Obesity Involves Alterations in Resting Energy Expenditure," J. Clin. Endocr. Metab. 89: 936-939, 2004.
Broglio, et al., "Non-Acylated Ghrelin Counteracts the Metabolic but not the Neuroendocrine Response to Acylated Ghrelin in Humans," The Journal of Clinical Endocrinology & Metabolism, vol. 69, No. 6, pp. 3062-3065, Jun. 2004.
Poykko, et al., "Low Plasma Ghrelin is Associated With Insulin Resistance, Hypertension, and the Prevalence of Type 2 Diabetes," Diabetes, vol. 52, pp. 2546-2553, Oct. 2003.
Soares, Joao-Bruno et al., "Ghrelin, des-acyl ghrelin and obestatin: three pieces of the same puzzle," Peptides, vol. 29, No. 7, Jul. 2008, pp. 1255-1270.

*Primary Examiner* — Gyan Chandra
(74) *Attorney, Agent, or Firm* — Fish & Richardson P.C.

(57) ABSTRACT

The present invention relates to compositions containing unacylated ghrelin and derivatives thereof and their uses in the control of glycemia in ageing patients, GH deficient patients, diabetic patients and obese patients.

8 Claims, 17 Drawing Sheets

METHODS FOR PROMOTING GROWTH AND SURVIVAL OF INSULIN-SECRETING CELLS

REFERENCE TO RELATED APPLICATIONS

This application is a divisional application of U.S. patent application Ser. No. 11/756,456 filed on May 31, 2007 which is a continuation-in-part of U.S. patent application Ser. No. 10/499,376, which has the international filing date of Dec. 18, 2002, and entered the U.S. national phase on Nov. 29, 2004, which U.S. patent application claims the benefit of priority of Canadian Patent Application No. 2,365,704, filed Dec. 18, 2001, the contents of which are herein incorporated by reference.

BACKGROUND OF THE INVENTION

1. Field of the Invention

This invention relates to new compositions comprising unacylated ghrelin and their therapeutical uses thereof.

2. Description of Prior Art

Ghrelin is a recently discovered gastric hormone of 28 amino acids showing a unique structure with an n-octanoyl ester at its third serine residue (Kojima M et al. Nature 1999; 402(6762):656660). Though many synthetic peptidyl and nonpeptidyl growth hormone (GH) secretagogues (GHS) were identified as ligands of GHS-R, ghrelin is shown to be a physiological ligand for the GHS-R. Ghrelin powerfully stimulates GH secretion through its interaction with GHS-R both in animals and in humans (Ukkola, O et al., 2002 Ann. Med. 34:102-108). The GH-releasing activity of ghrelin is mediated by activation of GHS-R at the pituitary and, mainly, at the hypothalamic level (Kojima M et al. Nature 1999; 402(6762):656660) likely by enhancing the activity of growth hormone releasing hormone (GHRH)-secreting neurons and, concomitantly, acting as a functional somatostatin (SS) antagonist (Ghigo E et al. Eur J Endocrinol 1997; 136 (5):445460). Other mechanisms have been postulated recently as well (Ahnfelt-Ronne I et al. Endocrine 2001; 14(1):133-135). The interplay among various factors leading to GH secretion is depicted in FIG. 1.

The GHS-R and its subtypes are not restricted to the hypothalamus-pituitary unit but are present also in other central and peripheral tissues (Papotti M et al. J Clin Endocrinol Metab 2000; 85(10):3803-3807) and the physiological actions of ghrelin, as well as those of synthetic GHS are not restricted to GH secretion. In fact, ghrelin stimulates lactotroph and corticotroph hormone secretion, has orexigenic and cardiovascular actions, shows anti proliferative effects on thyroid and breast tumors and regulates gastric motility and acid secretion through vagal mediation (Ukkola, O et al., 2002, Ann. Med. 34:102-108).

In humans, fasting leads to elevated serum GH concentrations. Traditionally, changes in hypothalamic GHRH and somatostatin have been considered as the main mechanisms, which induce elevations in GH secretion during fasting. As ghrelin administration in man also stimulates GH release, and serum ghrelin concentrations are elevated during fasting, increased ghrelin actions might be another mechanism whereby fasting results in the stimulation of GH release.

Although ghrelin is likely to regulate pituitary GH secretion in interplay with GHRH and SS, GHS receptors have also been identified on hypothalamic neurons and in the brainstem (Nakazato M et al. Nature 2001; 409(6817):194-198). Apart from potential paracrine effects, ghrelin may thus offer an endocrine link between the stomach, hypothalamus and pituitary, suggesting an involvement in the regulation of energy balance. Tschop et al. have shown that daily peripheral administration of ghrelin in mice and rats caused weight gain by reducing fat utilization (Tschop M et al. Nature 2000; 19; 407(6806):908-913). Intracerebroventricular administration of ghrelin generated a dose dependent increase in food intake and body weight. Rat serum ghrelin concentrations increased by fasting and decreased by re-feeding or oral glucose administration, but not by water ingestion. Apparently ghrelin, in addition to its role in regulating GH secretion, signals the hypothalamus when an increase in metabolic efficiency is necessary (Tschop M et al. Nature 2000; 19; 407(6806):908-913; Muller A F et al. Clin Endocrnol (Oxf) 2001; 55(4):461-467).

Studies by Kojima and others have shown that unacylated ghrelin (UAG) has no affinity to the known GHS-R (GHS-R1a receptor), which is responsible for GH release from the pituitary gland (Kojima M et al. Nature 1999; 402(6762):656-660). This was confirmed later by Bednarek M A et al (Bednarek M A et al, J. Med Chem. 2000, 43:4370-4376), who showed that unacylated ghrelin could not be a physiological ligand of the GHS-R1a receptor ($IC_{50}$>10,000 nM), since it poorly activated GHS-R1a at micromolar concentrations; large hydrophobic acyl group is obligatory at position 3 of ghrelin for its biological response on GH secretion.

The PCT application, WO 01/87335A2, discloses methods of selectively inhibiting ghrelin actions including those on obesity using growth hormone secretagogue receptor antagonists and ghrelin neutralizing reagents. The ghrelin neutralizing reagents are antibodies, single chain antibodies, antibody fragments, or antibody-based constructs.

Specific binding of acylated ghrelin can be found in many peripheral tissues (Papotti M et al. J Clin Endocrinol Metab 2000; 85(10):3803-3807). In these tissues, no mRNA expression of the GHS-R1a receptor could be found, indicating that other receptor (sub)types of receptors that can bind GHS would be responsible for this specific binding. These novel receptors may mediate ghrelin's peripheral actions which are, as shown in this invention, efficiently antagonized by unacylated ghrelin. These novel receptors may also mediate unacylated ghrelin direct actions on metabolism and cell proliferation, as shown in the present invention.

It would be highly desirable to be provided with pharmaceutical compositions of nonacylated ghrelin for glycemic control in certain metabolic diseases and disorders and methods to treat them.

SUMMARY OF THE INVENTION

In accordance with the present invention, there is provided a method for preventing and/or treating a metabolic disorder associated with impaired glucose metabolism in a patient comprising administering a therapeutically effective amount of an agent selected from the group consisting of an unacylated ghrelin, an analog thereof and a pharmaceutically acceptable salt thereof, to said patient.

In accordance with the present invention, there is provided a method as described above, wherein treatment of the metabolic disorder associated with impaired glucose metabolism is through enhancement of proliferation or of survival of insulin-secreting cells.

In accordance with the present invention, there is provided a method as described above, wherein the enhancement of proliferation or survival of insulin-secreting cells is achieved by administration of the unacylated ghrelin or the analog thereof in the patient.

In accordance with the present invention, there is provided a method as described above, wherein the enhancement of survival is achieved ex vivo by subjecting the insulin-secreting cells to the unacylated ghrelin or the analog thereof prior to administering said cells to the patient as a graft.

In accordance with the present invention, there is provided a method for enhancing survival and/or proliferation of insulin-secreting cells comprising culturing said cells in the presence of a therapeutically effective amount of an agent selected from the group consisting of unacylated ghrelin and an analog thereof.

In accordance with the present invention, there is provided a method for inhibiting death of insulin-secreting cells comprising culturing said cells in the presence of a therapeutically effective amount of an agent selected from the group consisting of unacylated ghrelin and an analog thereof.

In accordance with the present invention, there is provided a composition for preventing and/or reducing postprandial induction of insulin resistance comprising a therapeutically effective amount of at least one of unacylated ghrelin, an analog thereof and a pharmaceutically acceptable salt thereof in association with a pharmaceutically acceptable carrier.

The composition in accordance with a preferred embodiment of the present invention, wherein the unacylated ghrelin is having an amino acid as set forth in SEQ ID NO: 1.

In accordance with the present invention, there is provided a method for reducing postprandial induction of insulin resistance in a patient comprising the step of administering a therapeutically effective amount of the composition of the present invention to the patient.

The method in accordance with a preferred embodiment of the present invention, wherein the administration is through a route selected from the group consisting of intravenous, subcutaneous, transdermal, oral, buccal, sublingual, nasal and by inhalation.

The method in accordance with a preferred embodiment of the present invention, wherein the composition is administered in a dose varying from about 0.001 µg/kg to about 10.0 mg/kg, more preferably from about 1 µg/kg to about 1 mg/kg.

In accordance with the present invention, there is provided the use of the composition of the present invention for reducing postprandial induction of insulin resistance in a patient.

In accordance with the present invention, there is provided the use of the composition of the present invention for the preparation of a medicament for reducing postprandial induction of insulin resistance in a patient.

In accordance with the present invention, there is provided a composition for preventing and/or reducing dawn phenomenon in type I diabetes patient comprising a therapeutically effective amount of at least one of unacylated ghrelin, an analog thereof and a pharmaceutically acceptable salt thereof in association with a pharmaceutically acceptable carrier.

In accordance with the present invention, there is provided a method for preventing and/or reducing dawn phenomenon in type I diabetes patient comprising the step of administering a therapeutically effective amount of the composition of the present invention to the patient.

In accordance with the present invention, there is provided the use of the composition of the present invention for preventing and/or reducing dawn phenomenon in type I diabetes patient.

In accordance with the present invention, there is provided the use of the composition of the present invention for the preparation of a medicament for preventing and/or reducing dawn phenomenon in type I diabetes patient.

In accordance with the present invention, there is provided a composition for reducing body weight increased in a patient suffering from at least one of type II diabetes and syndrome X comprising a therapeutically effective amount of at least one of unacylated ghrelin, an analog thereof, and a pharmaceutically acceptable salt thereof in association with a pharmaceutically acceptable carrier.

The composition in accordance with a preferred embodiment of the present invention, wherein the patient is treated with oral antidiabetic drugs.

In accordance with the present invention, there is provided a method for reducing a body weight increased encountered by a patient suffering from at least one of type II diabetes and syndrome X comprising the step of administering a therapeutically effective amount of the composition of the present invention.

In accordance with the present invention, there is provided the use of the composition of the present invention for reducing a body weight increased encountered by a patient suffering from at least one of type II diabetes and syndrome X.

In accordance with the present invention, there is provided the use of the composition of the present invention for the preparation of a medicament for reducing a body weight increased encountered by a patient suffering from at least one of type II diabetes and syndrome X.

In accordance with the present invention, there is provided a composition for facilitating treatment of an insulin-resistant patient comprising a therapeutically effective amount of at least one of unacylated ghrelin, an analog thereof and a pharmaceutically acceptable salt thereof in association with a pharmaceutically acceptable carrier.

In accordance with the present invention, there is provided a method for facilitating the treatment of an insulin-resistant patient comprising the step of administering a therapeutically effective amount of the composition of the present invention to the patient.

In accordance with the present invention, there is provided the use of the composition of the present invention for facilitating the treatment of an insulin-resistant patient.

In accordance with the present invention, there is provided the use of the composition of the present invention for the preparation of a medicament for facilitating treatment of insulin-resistant patient.

In accordance with the present invention, there is provided a composition for decreasing fat mass in a growth hormone-deficient patient comprising a therapeutically effective amount of at least one of unacylated ghrelin, an analog thereof and a pharmaceutically acceptable salt thereof in association with a pharmaceutically acceptable carrier.

In accordance with the present invention, there is provided a method for decreasing fat mass in a growth hormone-deficient patient comprising the step of administering a therapeutically effective amount of the composition of the present invention to the patient.

In accordance with the present invention, there is provided the use of the composition of the present invention for decreasing fat mass in a growth hormone-deficient patient.

In accordance with the present invention, there is provided the use of the composition of the present invention for the preparation of a medicament for decreasing fat mass in a growth hormone-deficient patient.

In accordance with the present invention, there is provided a composition for decreasing fat mass in an ageing patient having a high body mass index comprising a therapeutically effective amount of at least one of unacylated ghrelin, an analog thereof and a pharmaceutically acceptable salt thereof in association with a pharmaceutically acceptable carrier.

In accordance with the present invention, there is provided a method for decreasing fat mass in an ageing patient having a high body mass index comprising the step of administering a therapeutically effective amount of the composition of the present invention to the patient.

In accordance with the present invention, there is provided the use of the composition of the present invention for decreasing fat mass in an ageing patient having a high body mass index.

In accordance with the present invention, there is provided the use of the composition of the present invention for the preparation of a medicament for decreasing fat mass in an ageing patient having a high body mass index.

In accordance with the present invention, there is provided a composition for preventing and/or reducing insulin resistance in a patient comprising a therapeutically effective amount of at least one of unacylated ghrelin, an analog thereof and a pharmaceutically acceptable salt thereof in association with a pharmaceutically acceptable carrier.

In accordance with the present invention, there is provided a method for preventing and/or reducing insulin resistance in a patient in severe catabolism comprising the step of administering to said patient a therapeutically effective amount of the composition of the present invention.

In accordance with the present invention, there is provided the use of the composition of the present invention for preventing and/or reducing insulin resistance in a patient in severe catabolism.

In accordance with the present invention, there is provided the use of the composition of the present invention for the preparation of a medicament for preventing and/or reducing insulin resistance in a patient in severe catabolism.

DETAILED DESCRIPTION OF THE INVENTION

Figure 1:
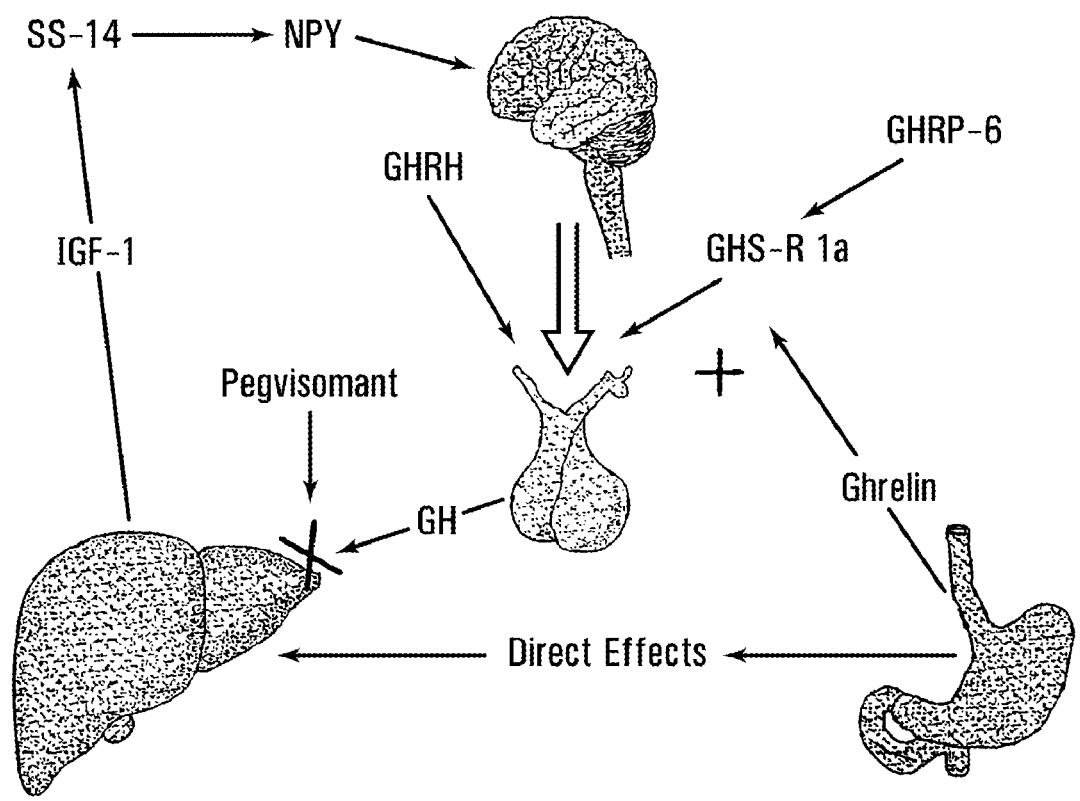
FIG. 1 illustrates the interplay among various factors leading to GH secretion.

Unless defined otherwise, all technical and scientific terms used herein have the same meaning as commonly understood by one of skill in the art to which the invention belongs.

In the present application, the terms "ghrelin" and "acylated ghrelin" are used interchangeably and are intended to mean the same.

For the purpose of the present invention the following terms are defined below.

The term "unacylated ghrelin" is intended to mean peptides that contain the amino acid sequence specified in SEQ ID NO: 1. Naturally-occurring variations of unacylated ghrelin include peptides that contain substitutions, additions or deletions of one or more amino acids which result due to discrete changes in the nucleotide sequence of the encoding ghrelin gene or its alleles thereof or due to alternative splicing of the transcribed RNA. It is understood that the said changes do not substantially affect the antagonistic properties, pharmacological and biological characteristics of unacylated ghrelin variant. Those peptides may be in the form of salts, particularly the acidic functions of the molecule may be replaced by a salt derivative thereof such as a trifuoroacetate salt.

The term "analogue of unacylated ghrelin" refers to both structural and functional analogues of unacylated ghrelin which are capable of replacing unacylated ghrelin in antagonizing the peripheral actions of ghrelin or in providing the same metabolic and cell proliferation effects as unacylated ghrelin. Simple structural analogues comprise peptides showing homology with unacylated ghrelin as set forth in SEQ ID NO: 1 or a fragment thereof. For example, an isoform of ghrelin-28 (SEQ ID NO: 1), des Gln-14 Ghrelin (a 27 amino acid peptide possessing serine 3 modification by n-octanoic acid) is shown to be present in stomach; it is functionally identical to ghrelin in that it binds to GHS-R1a with similar binding affinity, elicits $Ca^{2+}$ fluxes in cloned cells and induces GH secretion with similar potency as Ghrelin-28.

The term "homology" refers to sequence similarity between two peptides while retaining an equivalent biological activity. Homology can be determined by comparing each position in the aligned sequences. A degree of homology between amino acid sequences is a function of the number of identical or matching amino acids at positions shared by the sequences so that an "homologous sequence" refers to a sequence sharing homology and an equivalent function or biological activity.

It is known that des-Gln14-ghrelin is a structural analogue and a functional analogue of ghrelin; as such, unacylated des-Gln14-ghrelin could potentially antagonize effects of ghrelin and des-Gln14-ghrelin on peripheral metabolism involving insulin secretion and glycemic control, or provide the same direct biological effects as unacylated ghrelin on metabolism or cell proliferation and survival.

Functional analogues of unacylated ghrelin despite their diversity have the common interesting property of being able to fully replace unacylated ghrelin in one or more biological activities exhibited by unacylated ghrelin. For example, these biological activities of unacylated ghrelin may include, binding to a specific receptor, altering the signals arising from the activation of said receptor, modulating the functional consequences of activation of said receptor.

Functional analogues of unacylated ghrelin, as well as those of unacylated des-Gln14-ghrelin, are able to produce the biological effects of unacylated ghrelin, as described in the present application, hence such functional analogues will be useful for realizing therapeutic benefits in medical conditions involving GH-deficient states.

Conservative substitutions of one or more amino acids in the primary sequence of unacylated ghrelin may provide structural analogues of the peptide. In order to derive more potent analogues, it is customary to use alanine scans, selective substitutions with D-amino acid or synthetic amino acids, truncation of the peptide sequence in order to find a "functional core" of the peptide, covalent addition of molecules to improve the properties of the peptide such as its serum stability, in vivo half life, potency, hydrophilicity or hydrophobicity and immunogenicity.

General methods and synthetic strategies used in providing functional and structural analogues of peptides is described in publications such as "Solid phase peptide synthesis" by Stewart and Young, W. h Freeman & Co., San Francisco, 1969 and Erickson and Merrifield, "The Proteins" Vol. 2, p. 255 et seq. (Ed. Neurath and Hill), Academic Press, New York, 1976.

All documents referred to herein are hereby incorporated by reference.

In accordance with the present invention, there is provided pharmaceutical compositions for acting on insulin levels and glycemia in metabolic diseases and disorders and methods to prevent, reduce and treat them.

Figure 2A:
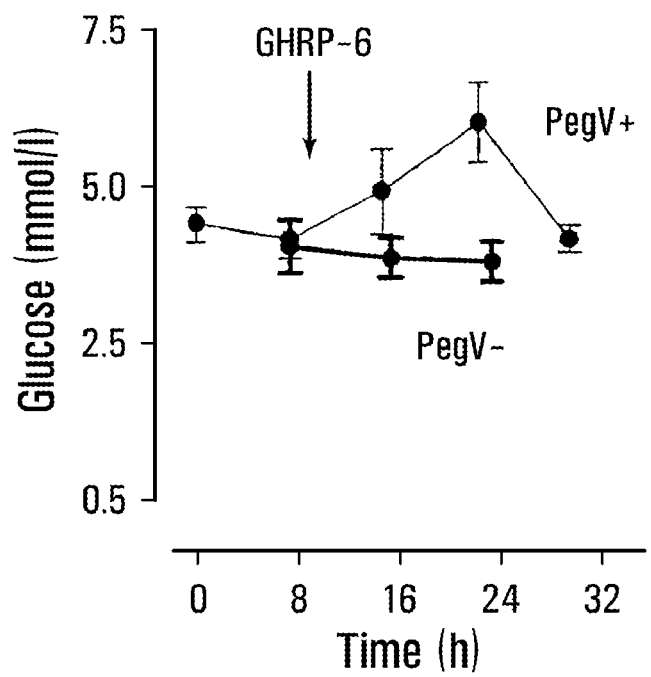
FIG. 2A illustrates glucose concentration over time in absence and in presence of the GH receptor antagonist pegvisomant upon administration of GHRP-6.
Figure 2B:
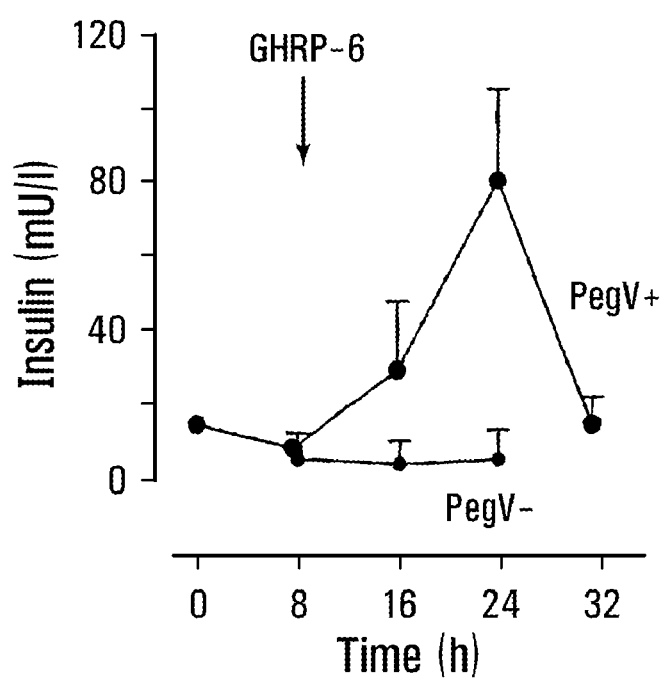
FIG. 2B illustrates insulin concentration over time in absence and in presence of the GH receptor antagonist pegvisomant upon administration of GHRP-6.

It has been demonstrated that the growth hormone secretagogue, GHRP-6, has direct and non-GH dependent actions on metabolism (Muller A F et al. J Clin Endocrinol Metab 2001; 86(2):590-593). It is shown in the present application that in normal human beings, preprandial GHS administration (1 μg/Kg i.v.) induces a postprandial increase in serum glucose levels, but only in the presence of the GH receptor antagonist pegvisomant (FIG. 2: left panel).

Moreover, this is accompanied by an impressive increase in serum insulin concentrations (indicating insulin resistance; FIG. 2A). These GHS-mediated changes indicate that when GH bioactivity is lowered (as seen in GH deficient, ageing, obese and diabetic individuals), GHS can induce potent changes in metabolic control, which are characteristic of the "metabolic syndrome X". Because in this study GH-action was blocked by pegvisomant, these GHS-mediated metabolic changes on the "gastro-entero-hepatic axis" must be direct and non-pituitary mediated. Supporting this hypothesis, daily ghrelin administration in rodents for only several days, indeed induces an obese state, again indicating that these GHS-mediated effects on metabolism are powerful and clinically relevant.

The data presented in the present application indicate that GHS-mediated effects are involved in the induction of the metabolic alterations, as well as subsequent changes in body composition, which are characteristic for the insulin resistance syndrome (metabolic syndrome), as observed in GH deficiency, but also during normal ageing, obesity and diabetes.

Figure 3:
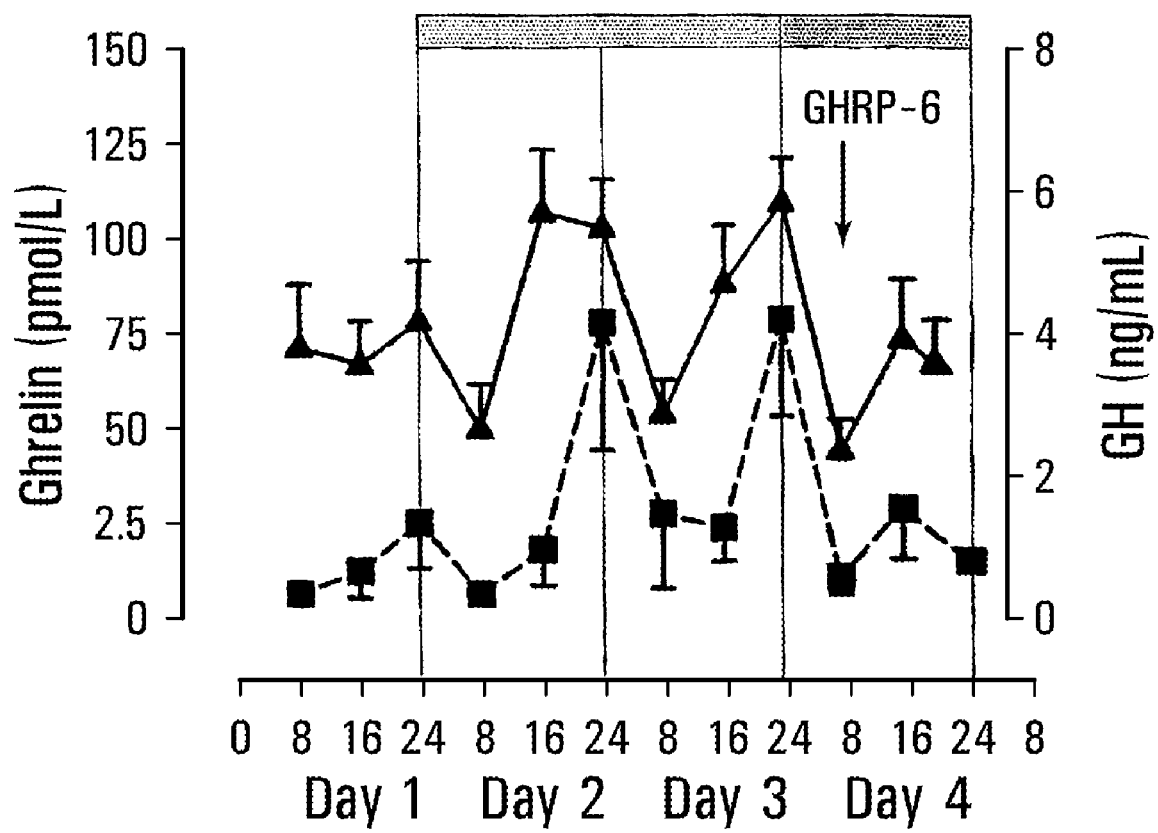
FIG. 3 illustrates the serum Ghrelin, and GH concentrations (Solid line: ghrelin levels; dotted line: GH levels) during fasting for three days and after a bolus injection of GHRP-6 on day 4.

In order to understand the diurnal rhythms of ghrelin and GH secretion during fasting, a study was conducted on 10 healthy human volunteers with normal body mass index. FIG. 3 shows the serum Ghrelin, and GH concentrations (Solid line: ghrelin levels; dotted line: GH levels) during fasting for three days and after a bolus injection of GHRP-6 on day 4. Fasting rapidly induces a diurnal ghrelin rhythm that is followed by a similar GH rhythm. Administration of 1 μg/kg of GHRP-6 on the 3rd day of fasting attenuated peak ghrelin levels in the afternoon. This clearly shows that fasting induces an acute and distinct diurnal rhythm in systemic ghrelin concentrations that is not present in the fed state. These changes in serum ghrelin levels during fasting are followed by similar changes in serum GH concentrations, indicating that ghrelin is the driving force of increased GH secretion during fasting. This phenomenon cannot be explained by changes in insulin, glucose or free fatty acid levels. Thus it appears that the metabolic effects of ghrelin are distinct from its effects on GH secretion.

By the use of the GH receptor antagonist pegvisomant, indirect evidence was provided that these changes in serum ghrelin levels are not regulated by the GH receptor. Finally, it was shown that administration of the synthetic GHS, GHRP-6, produced a decrease in peak ghrelin levels, but this effect was only observed after several hours, indicating the existence of a long-loop feedback system of GHS's on ghrelin secretion.

Figure 4A:
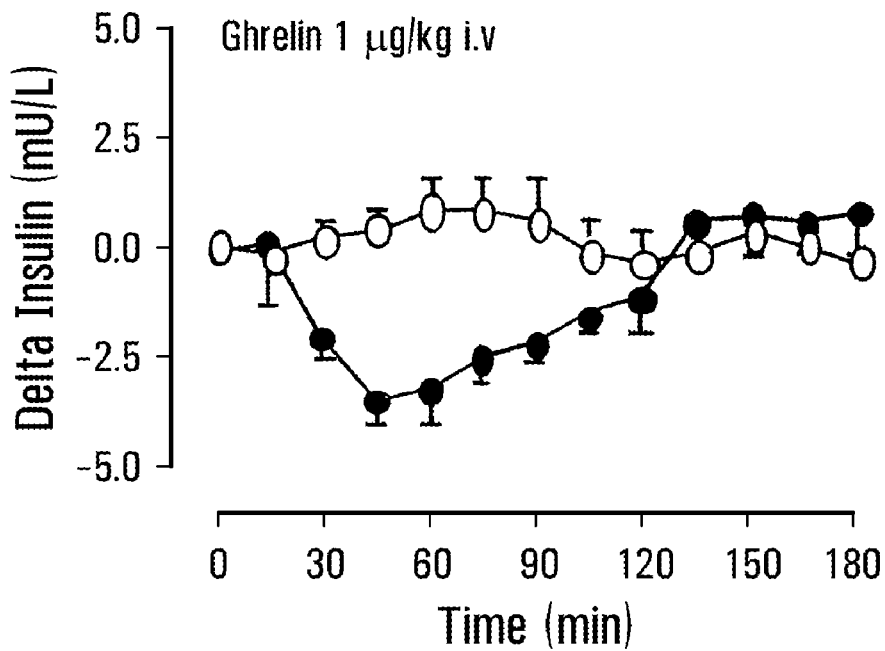
FIG. 4A illustrates insulin variation over time in a patient having received a single intravenous administration of human ghrelin (solid dots) or placebo (open dots)
Figure 4B:
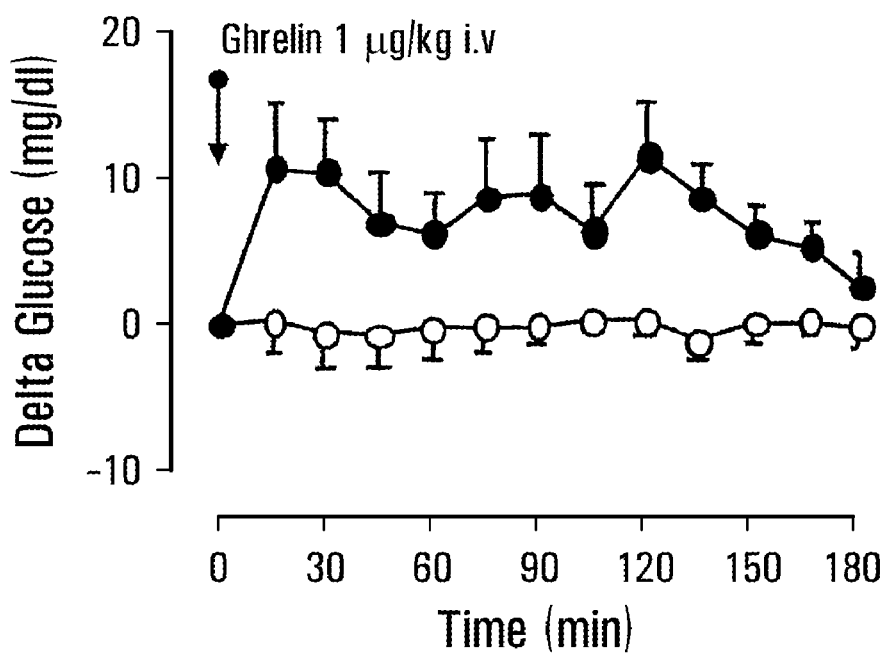
FIG. 4B illustrates glucose variation over time in a patient having received a single intravenous administration of human ghrelin (solid dots) or placebo (open dots)

In order to elucidate the metabolic effects of ghrelin, a study was performed on 11 healthy young male volunteers in whom glucose and insulin levels were measured after a single intravenous administration of human ghrelin (1.0 μg/kg i.v. at 0') or placebo. FIG. 4 shows that ghrelin produced acute decrease in insulin [mean (±SEM) Δ insulin] (top panel) and elevation in glucose [δ mean (±SEM) glucose] levels (bottom panel) (solid dots: ghrelin; open dots: placebo). This data clearly shows that ghrelin has distinct and immediate effects on glucose and insulin, two important determinants of metabolism in humans (Broglio F et al. Journal of Clinical Endocrinology & Metabolism 2001; 86(10):5083-5086).

Thus the data reported in the present application, indicate that to ghrelin has important physiological actions, not only on GH secretion but also on the modification of glucose and insulin concentrations in living (human or animal) beings.

Ghrelin appears to have a role in managing not only GH secretion but also the metabolic response to starvation by modulating insulin secretion and glucose metabolism.

In an analysis of a study in normal human volunteers (n=6), it was surprisingly observed that the administration of unacylated ghrelin (1 μg/kg iv at 0 min) totally prevented the ghrelin (1 μg/kg iv at 0 min)-induced increase in glucose and decrease in insulin levels. The lots of unacylated ghrelin used in this study had the following specifications: tifluoroacetate salt of unacylated ghrelin, 95.1% pure as judged by HPLC, Mass: 3244.7 amu, and the peptide has amino acid composition representative of the sequence listed in SEQ ID NO: 1.

Figure 5A:
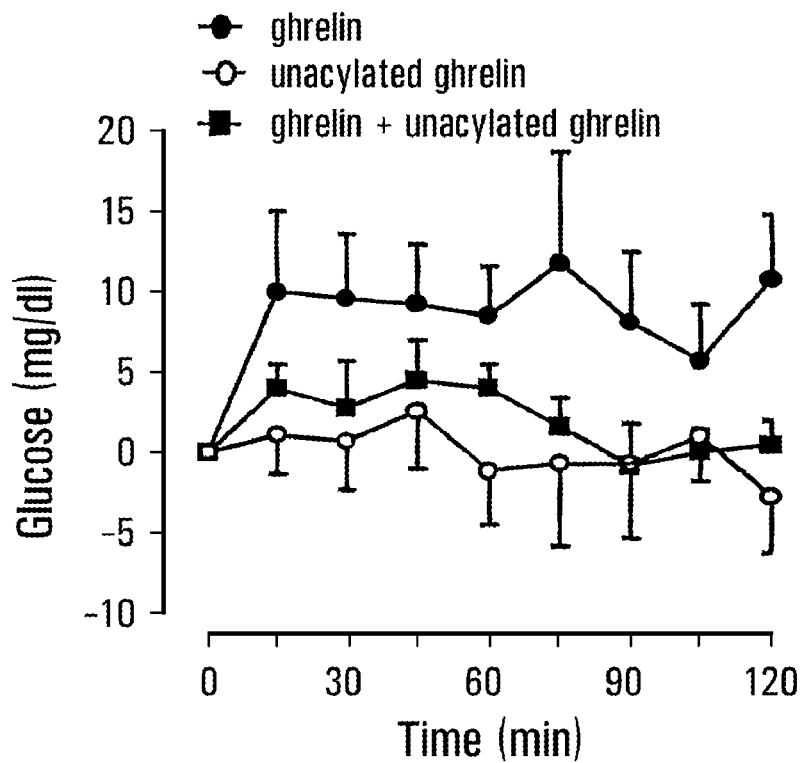
FIG. 5A illustrates glucose level over time in a patient having been administered with ghrelin, desoct-ghrelin or ghrelin and desoct-ghrelin.
Figure 5B:
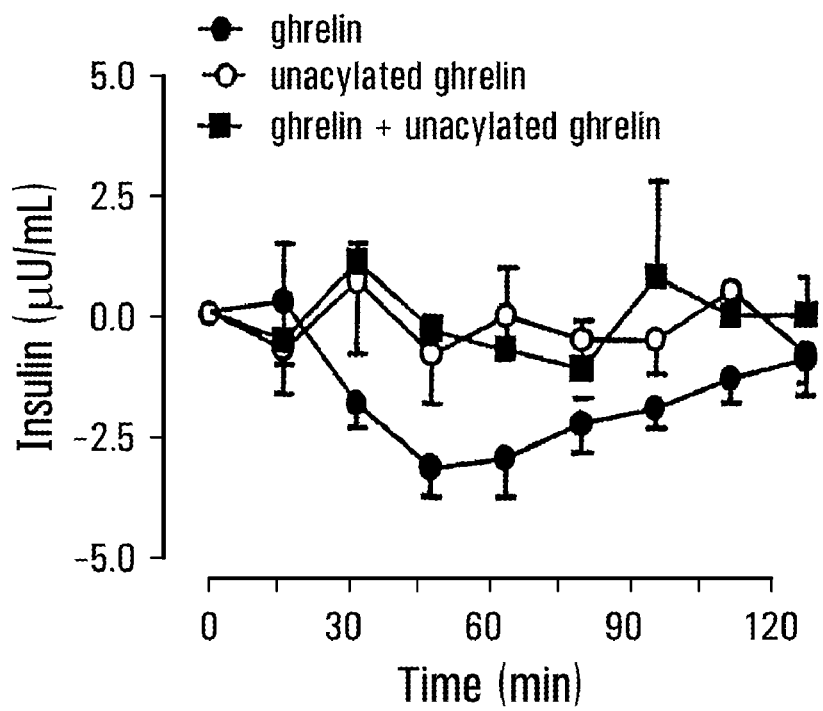
FIG. 5B illustrates insulin level over time in a patient having been administered with ghrelin, desoct-ghrelin or ghrelin and desoct-ghrelin.

FIGS. 5A-5B show the mean (±SEM) Δ glucose (FIG. 5A) and Δ insulin (FIG. 5B) levels after a single intravenous administration of human acylated ghrelin (1.0 μg/kg i.v. at 0'), human des-acylated ghrelin (1.0 μg/kg i.v. at 0') or the co-administration of both. Thus it appears that unacylated ghrelin is acting as a functional antagonist of the peripheral actions of ghrelin. This last result was surprising and unexpected, since unacylated ghrelin has never been shown previously to antagonize or inhibit the biological effects of acylated ghrelin. Most of ghrelin actions, especially on GH secretion were thought to be mediated by GHS-R1a receptor for which unacylated ghrelin has little affinity. In fact, unacylated ghrelin has so far been considered as a peptide without any biological activity.

Hence in this invention, it is shown that unacylated ghrelin acts as a functional antagonist to inhibit important peripheral actions of acylated ghrelin on two crucial parameters of metabolism-insulin and glucose. To provide therapeutic benefits to patients in various states of impaired glucose metabolism and/or insulin resistance, preferably those associated with low GH action and/or increased acylated ghrelin secretion, unacylated ghrelin (NH$_2$Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg: SEQ ID NO: 1) or its analogue may be administered in a pharmaceutical composition intravenously, subcutaneously, transdermally, orally or by inhalation. Preparation of pharmaceutical compositions suitable for intravenous, subcutaneous, transdermal, oral, buccal, sublingual and pulmonary delivery are known to people skilled in the arts.

In this invention it is also demonstrated that unacylated ghrelin has a direct influence on glucose and on lipid metabolism, and on the proliferation and survival of beta cells.

In one aspect of the invention, the effects of unacylated ghrelin (1.0 μg/Kg/h infused iv for 16 consecutive hours from 21.00 to 13.00 h) or saline was evaluated in 8 healthy males (age mean±SEM:29.6±2.4 yrs; BMI:22.4±1.7 kg/m$^2$) who had isocaloric balanced fixed meals at 21.20 and 09.00 h. Glucose, insulin, glucagon, free fatty acids (FFA), GH, and cortisol were measured every 20 minutes.

Figure 6A:
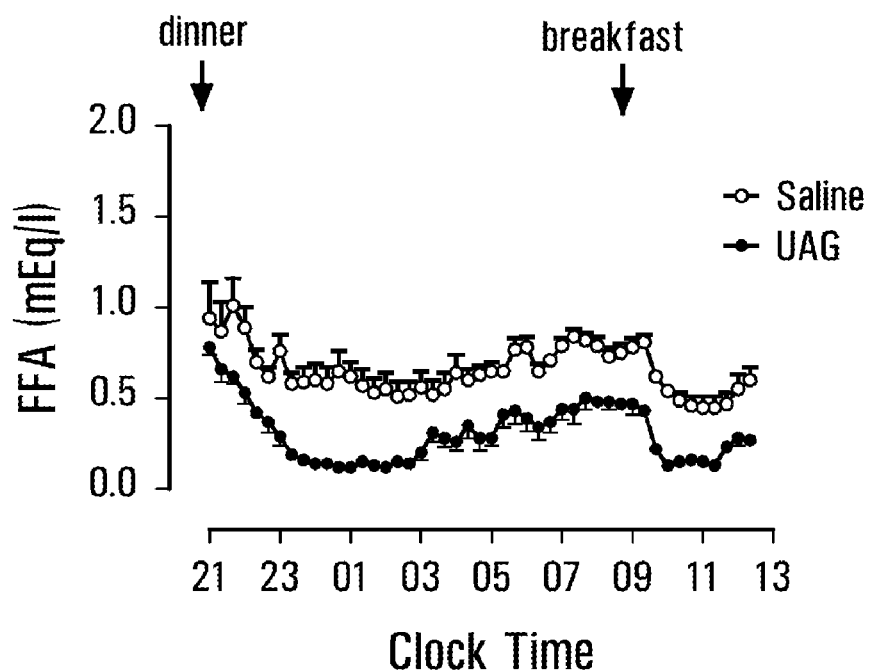
FIGS. 6A and 6B illustrate the free fatty acid (FFA) profile and AUC during saline or unacylated ghrelin infusion (1.0 μg/Kg/h, from 21.00 to 13.00 h) in healthy subjects.
Figure 6B:
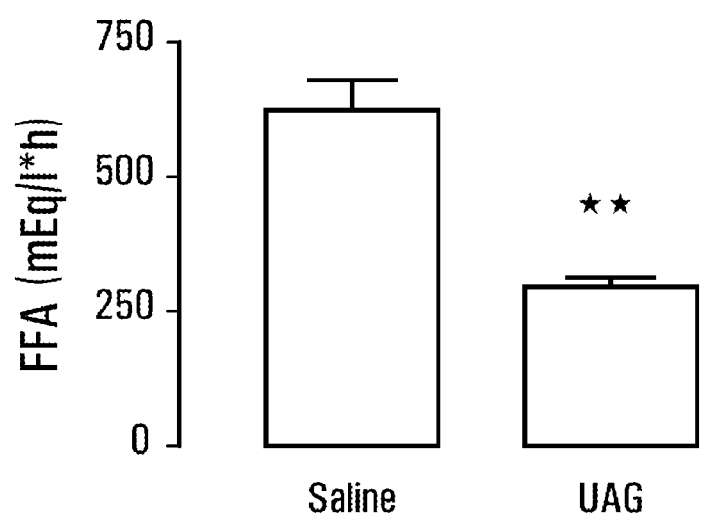
Figure 6C:
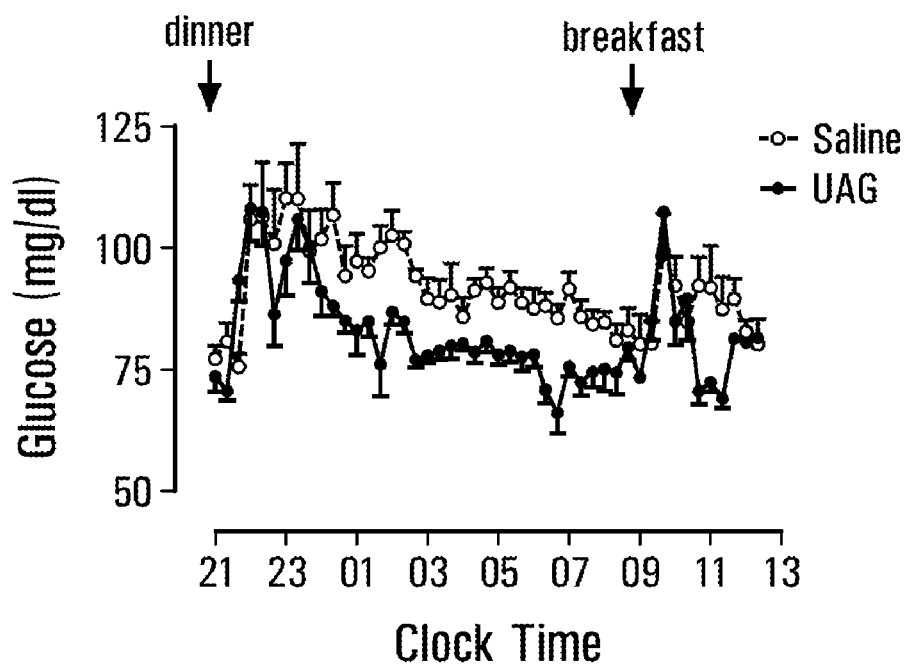
FIGS. 6C and 6D illustrate glucose profile and AUC during saline or unacylated ghrelin infusion (1.0 μg/Kg/h, from 21.00 to 13.00 h) in healthy subjects.
Figure 6D:
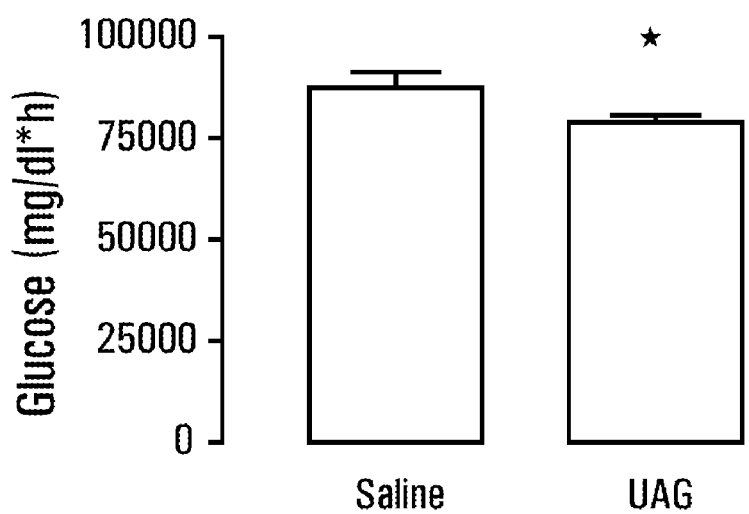
Figure 6E:
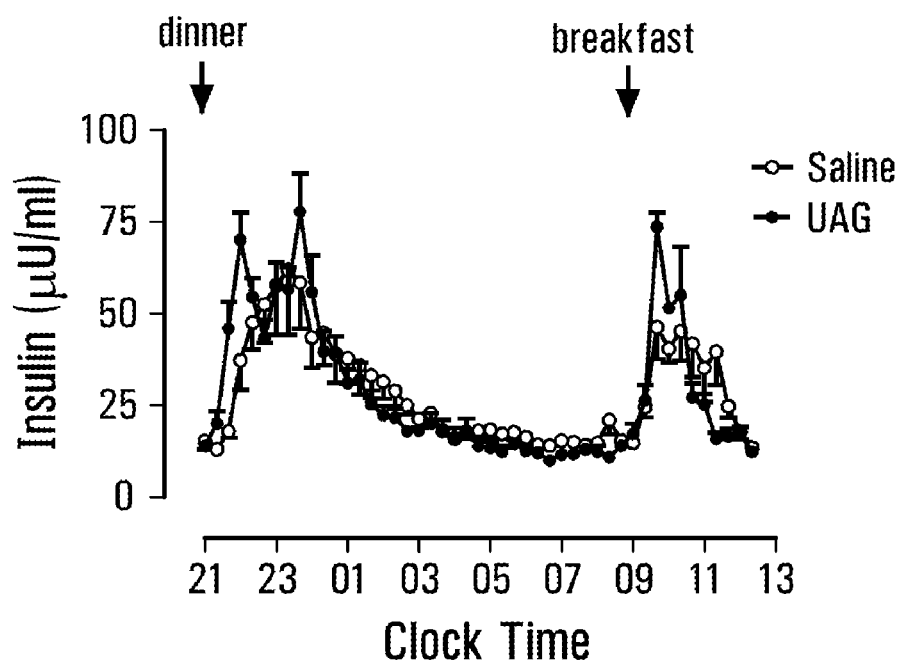
FIG. 6E illustrates insulin and FIG. 6F illustrates glucagon profile during saline or unacylated ghrelin infusion (1.0 μg/Kg/h, from 21.00 to 13.00 h) in healthy subjects.
Figure 6F:
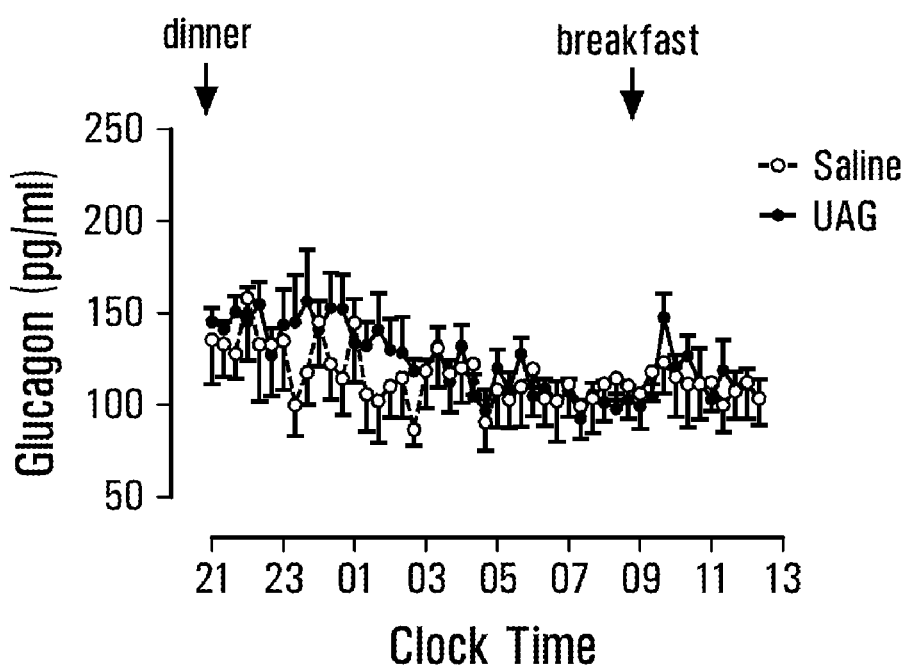
Figure 6G:
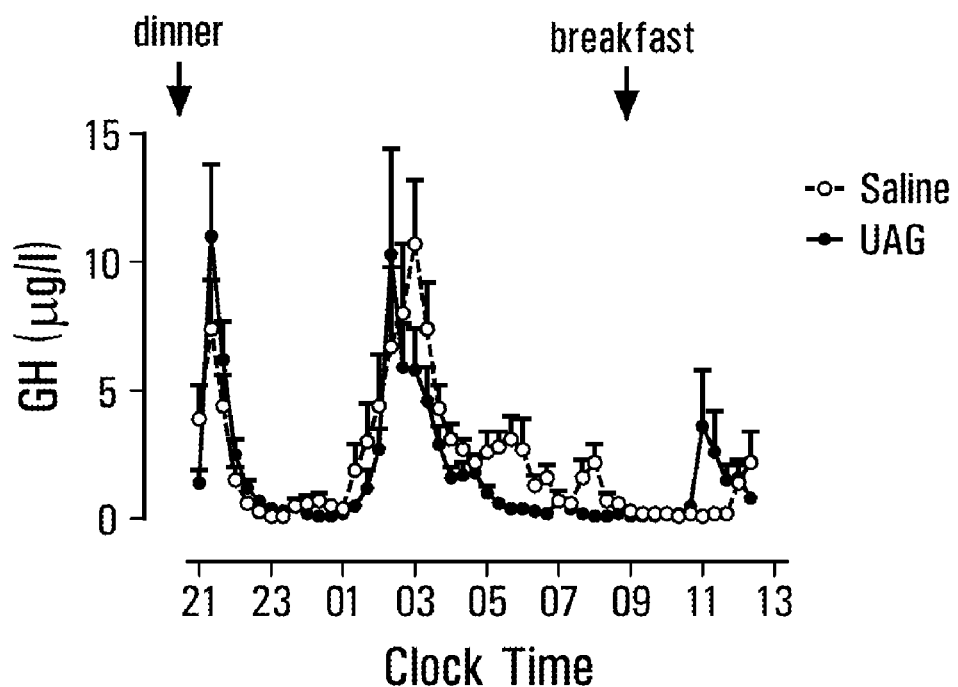
FIG. 6G illustrates growth hormone (GH) and FIG. 6H illustrates cortisol profile during saline or unacylated ghrelin infusion (1.0 μg/Kg/h, from 21.00 to 13.00 h) in healthy subjects.
Figure 6H:
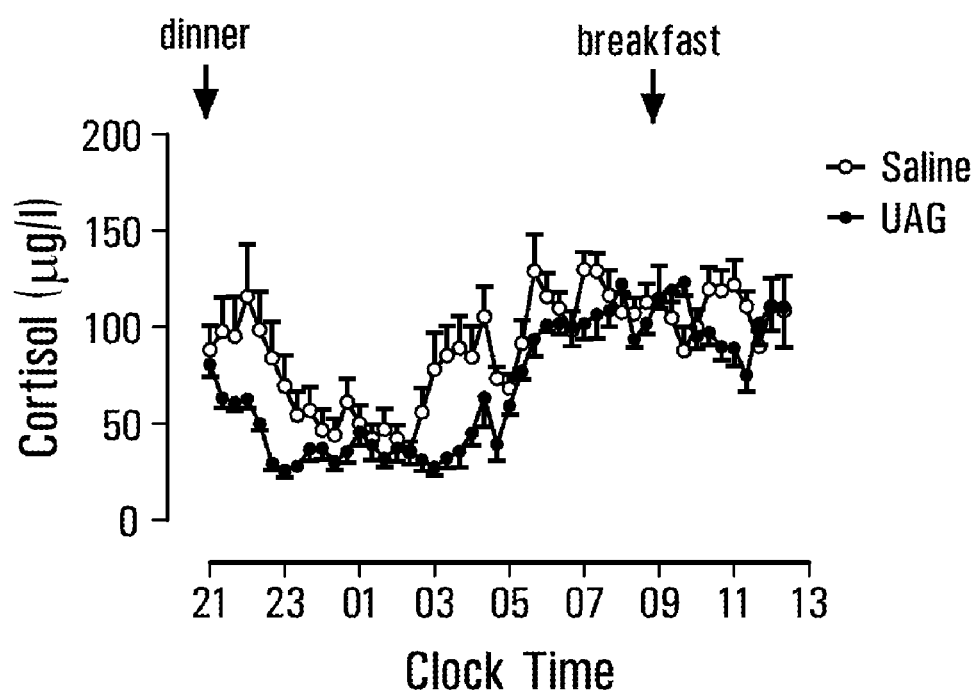

Unacylated ghrelin infusion significantly modified the profile of all parameters, except glucagon. Compared to saline, unacylated ghrelin decreased free fatty acyl (FFA) and glucose AUCs (p<0.01) (FIGS. 6A to 6D). The FFA profile was reduced both post-prandially (p<0.01) and at fasting (p<0.01), while glucose decrease during unacylated ghrelin was particularly relevant at fasting during night time (p<0.01) (FIGS. 6A to 6D). Unacylated ghrelin did not modify total insulin AUC, which, altogether with the significant reduction in glucose levels, indicated improved insulin sensitivity; however the early insulin response to both dinner (p<0.01) and breakfast (p<0.05) was enhanced by unacylated ghrelin (FIGS. 6E and 6F). During unacylated ghrelin infusion, cortisol and GH AUCs were lower (p<0.01) than those during saline, but cortisol remained within physiological levels) (FIGS. 6G and 6H). Since both cortisol and growth hormone are hyperglycemic hormones, their reduction under unacylated ghrelin infusion very likely also contributed to the observed glycemia-lowering effect.

The intravenous infusion of unacylated ghrelin in normal subjects enhances the early insulin response to meals, improves glucose metabolism and insulin sensitivity, and decreases circulating free fatty acids levels. Thus, unacylated ghrelin displays a remarkable metabolic impact, a promising anti-diabetogenic action through an original mechanism of action.

Survival of pancreatic β-cells is obviously of major importance for maintaining normal glucose metabolism. Apoptosis of pancreatic β-cells is a critical step in the development of type 1 diabetes, but β-cell growth and survival are critical also in type 2 diabetes. Inflammatory cytokines, including IFN-γ, TNF-α, and IL-1β are strongly implicated in pancreatic islet β-cell death and functional loss during autoimmune diabetes and also seem to be involved in early loss of islet mass in islet transplantation.

Unacylated ghrelin immunoreactivity was detected in HIT-T15 β-cells. Moreover, these cells were analyzed for their capacity of releasing unacylated ghrelin. ELISA experiments demonstrated that unacylated ghrelin was secreted by HIT-T15 cells (185 and 242 pg/ml, respectively) after 48 h incubation in complete medium. No expression of GRLN-R could be detected in HIT-T15 cells, either at the protein or at the mRNA level. HIT-T15 cells express ghrelin mRNA and peptide but not GRLN-R (not shown).

Figure 7:
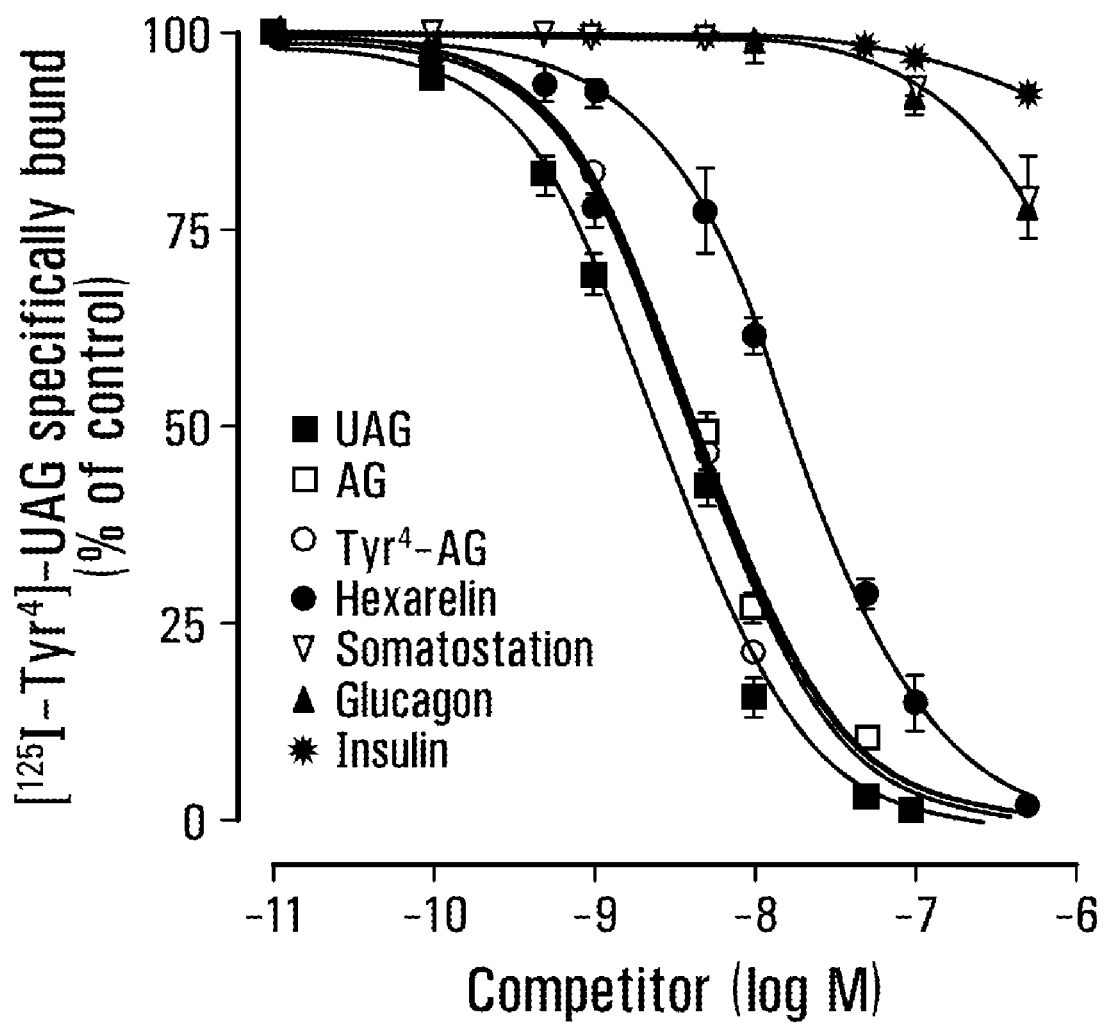
FIG. 7 illustrates a competition for radiolabeled unacylated ghrelin ($[^{125}I\text{-Tyr}^4]$-unacylated ghrelin) to HIT-T15 cell membranes by the indicated competitors. Binding is expressed as percentage of control (specific binding in the absence of unlabeled competitor)

Experiments using increasing concentrations of $^{125}$I-labeled [Tyr$^4$]-unacylated ghrelin provided consistent evidence of a saturable specific binding in HIT-T15 cells (FIG. 7). Scatchard analysis (not shown) demonstrated the existence of a single class of binding sites that showed values of $B_{max}$ (13.9±0.8 fmol/mg protein) and Kd (0.68±0.10 nm, mean±sem of four independent experiments). Unlabeled unacylated ghrelin, as well as [Tyr$^4$]-acylated ghrelin and hexarelin, but not somatostatin, insulin, or glucagon competed with $^{125}$-labeled [Tyr$^4$]-unacylated ghrelin for binding sites. Unacylated ghrelin recognizes common high-affinity binding sites on HIT-T15 cell membranes.

Figure 8A:
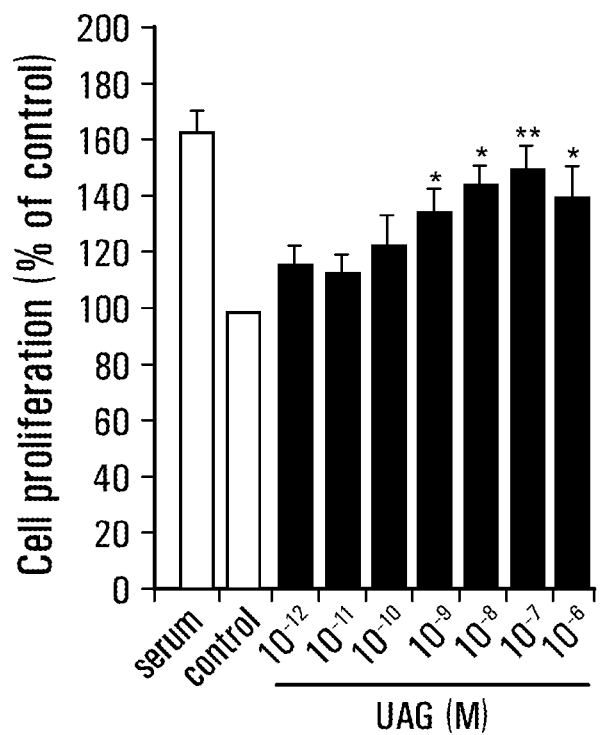
FIG. 8A illustrates HIT-T15 cell proliferation in the presence of increasing concentration of unacylated ghrelin.
Figure 8B:
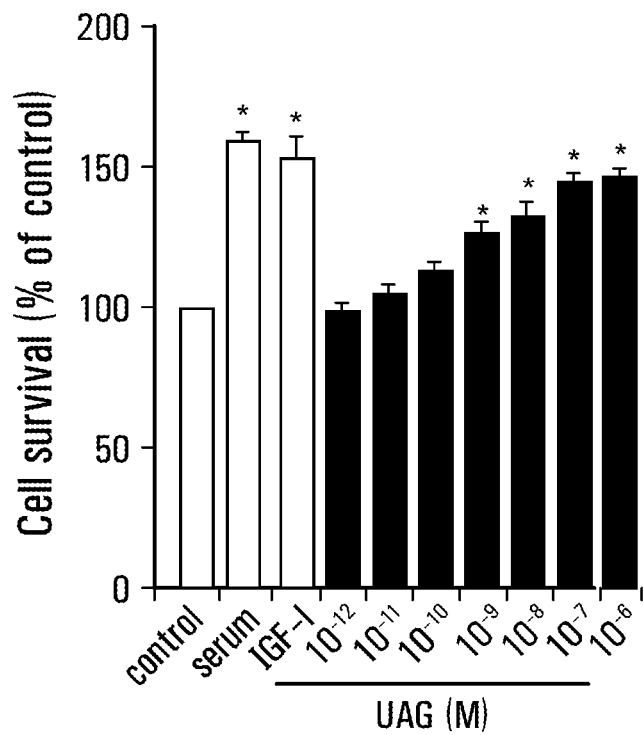
FIG. 8B illustrates HIT-T15 cell survival in the presence of increasing concentration of unacylated ghrelin.

Based on evidence of unacylated ghrelin-specific binding sites, the effect of unacylated ghrelin on HIT-T15 cell proliferation was investigated. In one variant of the invention, cells were incubated in serum-free medium in the presence or absence of increasing concentrations, ranging from 1 pm to 1 μm ($10^{-12}$ to $10^{-6}$ m) of unacylated ghrelin for 24 h, BrdU incorporation assay showed that the peptide significantly and dose-dependently induced cell proliferation (FIGS. 8A and 8B). The efficacy of cell growth stimulation was within 1 nm to 1 μm, equal to the one that was found effective in displacing radiolabeled unacylated ghrelin from HIT-T15 binding sites. This effect was similar to that observed in cells cultured in normal conditions, i.e. in the presence of serum (15% HS, 2.5% FBS).

Figure 8C:
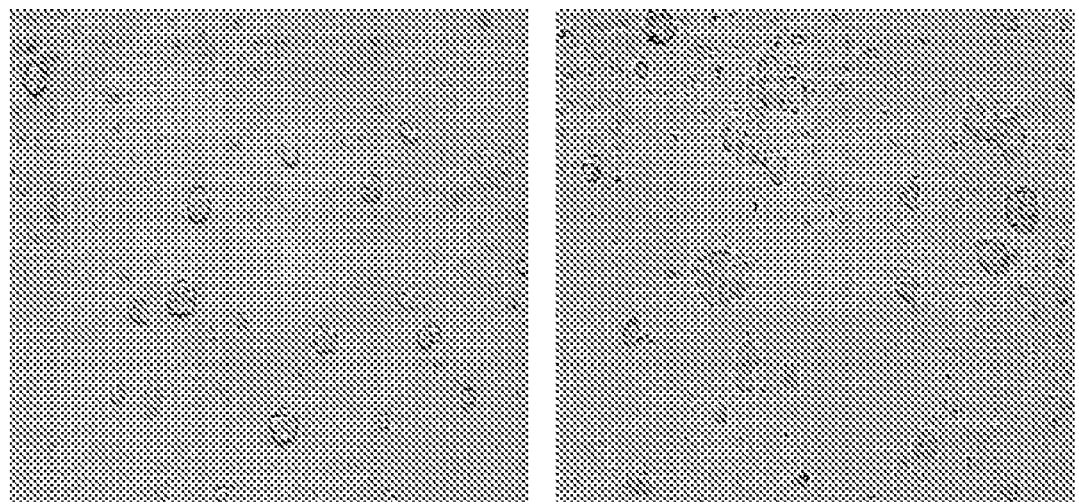
FIG. 8C illustrates phase-contrast images of cells cultured in the presence or absence of unacylated ghrelin.
Figure 8D:
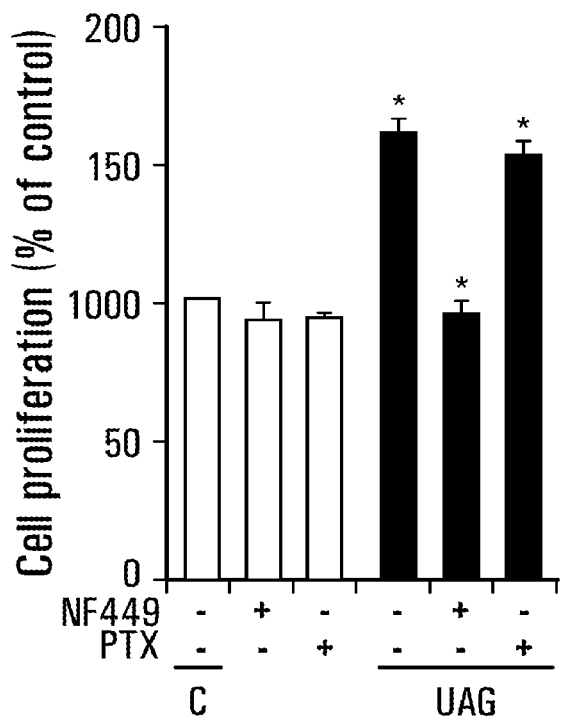
FIG. 8D illustrates effect of unacylated ghrelin on HIT-T15 cell proliferation in the presence of NF499 or pertussis toxin (PTX)
Figure 8E:
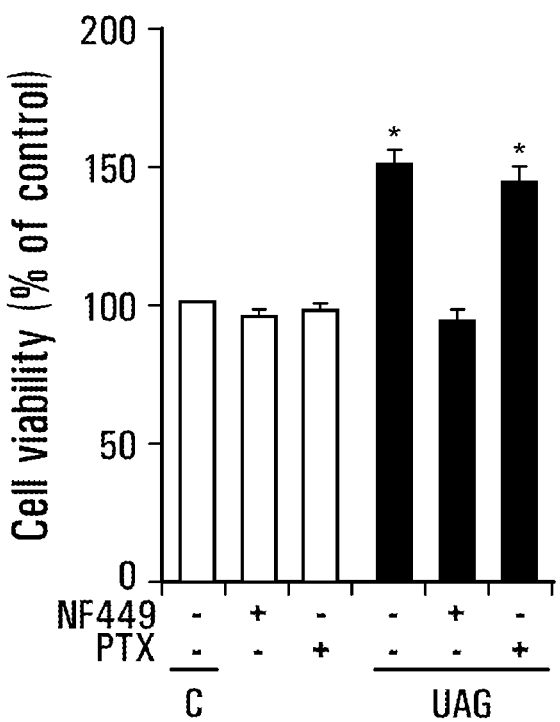
FIG. 8E illustrates the effect of unacylated ghrelin on HIT-T15 cell viability in the presence of NF499 or pertussis toxin (PTX)

To investigate the signaling pathways involved in ghrelin mitogenic effect, the cells were preincubated (30 min) with NF449, a selective Gα$_s$ protein-coupled receptor antagonist. This resulted in complete blockade of unacylated ghrelin-induced cell proliferation, whereas pretreatment with pertussis toxin (PTX; 50 ng/ml), an inhibitor of $G\alpha_{i/o}$ protein coupled receptor, had no effect (FIGS. 8D-8E). FIG. 8C is a representative phase contrast image showing that unacylated ghrelin counteracts HIT-T15 β-cell loss in serum deprived conditions by increasing the number and size of islet-like structures, with respect to untreated cells. Taken together, these results show that unaclylated ghrelin promotes β-cell proliferation, likely involving the $G\alpha_s$ signaling pathway.

In FIG. 8A to 8E, HIT-T15 cells were cultured in serum-free medium (Control) for 24 h, UAG alone or with NF449 and pertussis toxin (PTX) were added to the incubation medium for further 24 h. In FIG. 8A, cell proliferation was measured by BrdU uptake in cells cultured in the presence or absence of serum, UAG at the concentrations indicated. In FIG. 8B, cell survival was measured by MTT in the presence or absence of serum, IGF-I (15 nM), unacylated ghrelin at the concentrations indicated. FIG. 8C illustrates a phase-contrast images of cells cultured±unacylated ghrelin (100 nM each). FIG. 8D and FIG. 8E illustrate unacylated ghrelin proliferative and survival effect (100 nM each), assessed by BrdU and MTT respectively, in the presence of NF499 (10 μM) or pertussis toxin (PTX) (50 ng/ml), (C, control). Data are expressed as the percentage relative to control and are the means±SEM of eight replicates within a single representative experiment that was repeated at least 3 times (*$P<0.05$, **$P<0.01$).

Figure 9A:
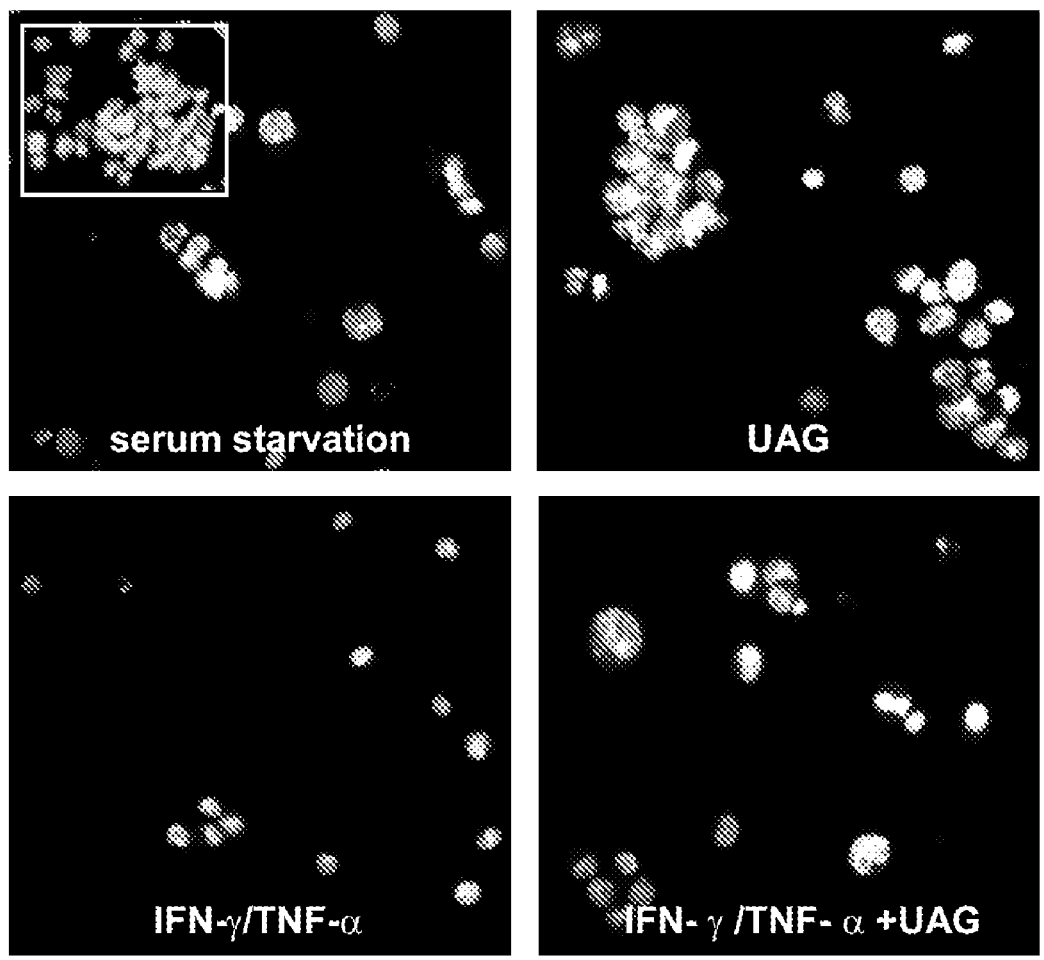
FIG. 9A illustrates a Hoechst 33258 nuclear immunofluorescence staining of serum starved cells±unacylated ghrelin (upper panel) and cells treated with IFN-γ/TNF-α±unacylated ghrelin (lower panel)
Figure 9B:
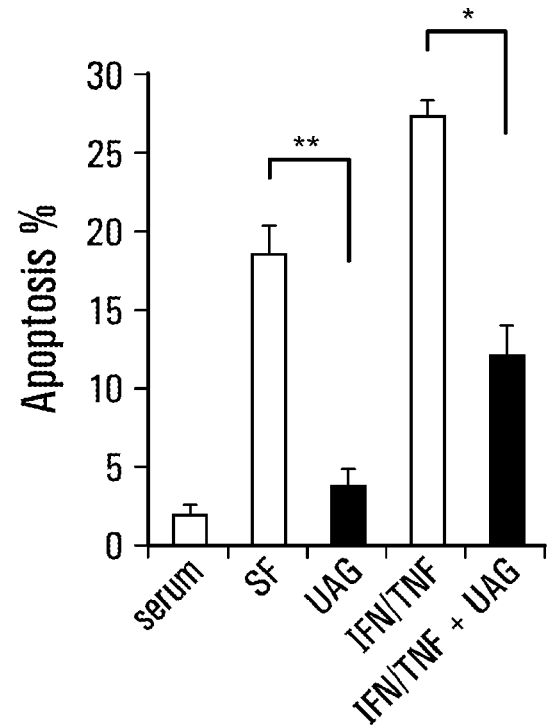
FIG. 9B illustrates the effect of unacylated ghrelin on apoptosis induced by serum starvation and IFN-γ/TNF-α synergism in HIT-T15 cells.

Apoptosis is the main form of pancreatic β-cell death in animal models of type 1 diabetes mellitus. IFN-γ/TNF-α synergism has been shown to play an important role in autoimmune diabetes in vivo as well as β-cell apoptosis in vitro. On the basis of the results showing that unacylated ghrelin promotes HIT-T15 cell proliferation, it was examined whether unacylated ghrelin inhibited apoptosis induced by serum deprivation or by IFN-γ/TNF-α synergism. Hoechst 33258 staining showed that after 48 h, cells cultured in the presence of serum were round shaped, formed islet-like structures, and had very low apoptotic rate (~2%) (FIG. 9A inset, upper panel, and FIG. 9B). In serum-deprived medium, apoptosis increased up to approximately 20%, and cells displayed typical chromatin condensation and nuclear fragmentation. Moreover, they partially lost their capacity to form islet-like structures (FIG. 9A, upper panel, and 9B). Cytokines further increased apoptosis (~27%), cells appearing smaller and unable to form islets (FIG. 9A, lower panel, and FIG. 9B). Although effects on glucagon and insulin release have been demonstrated with ghrelin at low concentrations (<100 nm), on the basis of binding studies and cell proliferation results, 100 nm ($10^{-7}$ m) was selected as the preferred unacylated ghrelin concentration for the continuation of this study. Accordingly, others have reported that ghrelin exerts proliferative and antiapoptotic effects at high concentrations (100-1000 nm) in different cell types. Unacylated ghrelin, preferably at 100 nm, almost completely prevented serum-starvation-induced apoptosis and restored islet-like structures (FIG. 9A, upper panel, and FIG. 9B). Unacylated ghrelin significantly reduced apoptosis (~12%) triggered by the IFN-γ/TNF-α combination and induced cell enlargement and small islet formation (FIG. 9A, lower panel, and FIG. 9B).

The unacylated ghrelin antiapoptotic effect was dose dependent, 1 nm ($10^{-9}$ m) being the lowest significantly active concentration of peptides (data not shown). Furthermore, caspase-3 activation in both serum-starved and cytokine-treated cells was significantly reduced by unacylated ghrelin (data not shown) providing additional evidence of its antiapoptotic effect in HIT-T15 pancreatic β-cells.

Figure 9C:
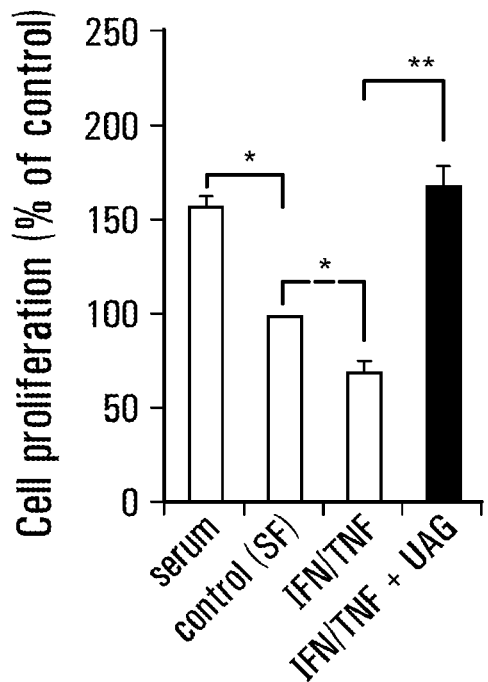
FIG. 9C illustrates the effect of unacylated ghrelin on cell proliferation of HIT-T15 cells induced by serum starvation and IFN-γ/TNF-α synergism.

Indeed, cytokines strongly decreased cell proliferation, and unexpectedly, unacylated ghrelin dramatically restored cell proliferation up to rates that were even higher than those observed in the presence of serum (FIG. 9C). Unacylated ghrelin effect on cell survival was also investigated by MTT assay in both serum-free conditions and in the presence of cytokines. The results of these experiments indicated that unaclylated ghrelin significantly increased cell viability under both experimental conditions (data not shown).

Figure 9D:
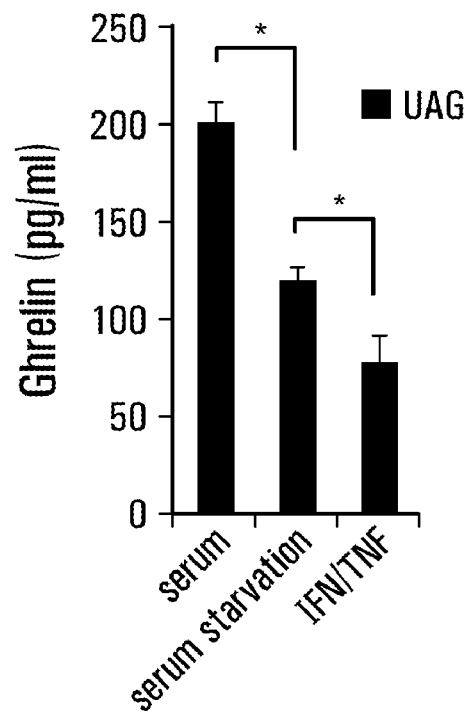
FIG. 9D illustrates unacylated ghrelin secretion in HIT-T15 cells following exposure to either serum, SF±cytokines.

Herein, it was previously showed that HIT-T15 cells express and release unacylated ghrelin, indicating that it could act through autocrine/paracrine mechanisms. To investigate this possibility, unacylated ghrelin secretion was measured in cells cultured in the presence of serum and in serum-free medium alone or with addition of IFN-γ/TNF-α. FIG. 9D shows that unaclylated ghrelin level was significantly reduced in serum-starved cells and even more after exposure to cytokines. Surprisingly, addition of a specific antighrelin antibody with specificity for unacylated ghrelin not only increased serum starvation-induced apoptosis but also induced apoptosis in cells cultured in the presence of serum, suggesting that endogenous unacylated ghrelin could exert autocrine/paracrine action on cell survival. As expected, no effect was observed in cytokine-induced apoptosis, where unacylated ghrelin secretion is likely too low to counteract such a strong cell death increase (FIG. 9E).

Figure 9E:
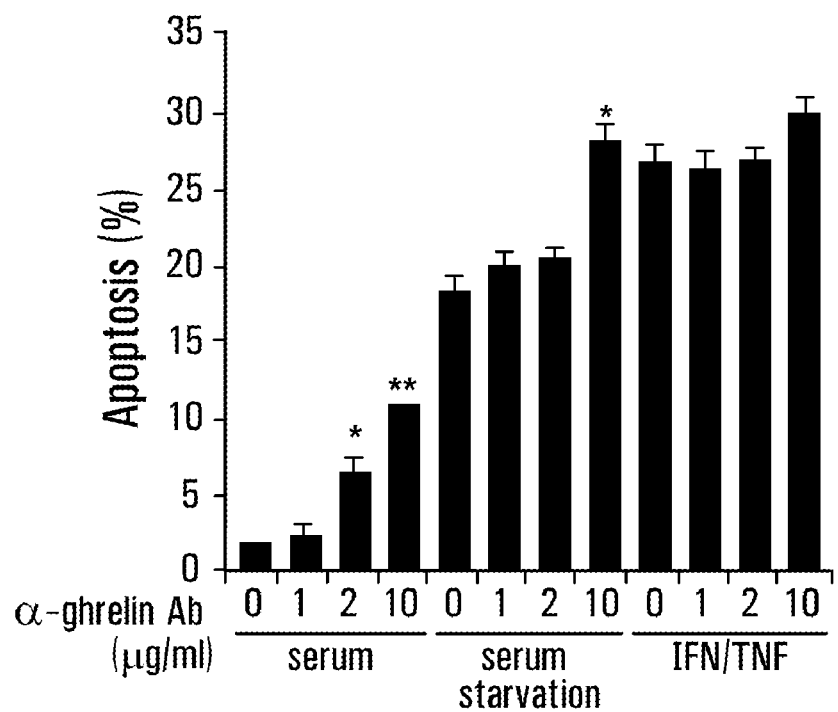
FIG. 9E illustrates a Hoechst 33258 of cells cultured for 48 h in the presence of serum or in SF medium alone with addition of an anti-ghrelin antibody.

In FIGS. 9A to 9E, HIT-T15 cells were starved for 24 h and subsequently incubated for 24 h in the presence or absence of IFN-γ/TNF-α (100 ng/ml and 200 ng/ml respectively), 100 nM unacylated ghrelin. FIG. 9A illustrates a Hoechst 33258 nuclear immunofluorescence staining (magnification ×200) of serum starved cells±unacylated ghrelin (upper panel; insert: cells with serum) and cells treated with IFN-γ/TNF-α±unacylated ghrelin (lower panel). In FIG. 9B, apoptosis is evaluated by counting condensed/fragmented Hoechst-stained nuclei (SF, serum-free medium). Values are expressed as percent of apoptotic cells and are the mean±SEM of duplicate determinations (500 cells each) of three independent experiments (*$P<0.05$; **$P<0.01$). In FIG. 9C, cell proliferation is assessed by BrdU uptake (ELISA). The results are expressed as percent of control (serum starved cells) and are the mean±SEM of three independent experiments (*$P<0.05$, **$P<0.01$). FIG. 9D illustrates ghrelin secretion in HIT-T15 conditioned medium following exposure to either serum, SF±cytokines. The results are the mean±SEM of three independent experiments, each performed in quadruplicate (*$P<0.05$). In FIG. 9E, apoptosis is determined by Hoechst 33258 of cells cultured for 48 h in the presence of serum or in SF medium alone with addition of an anti-ghrelin antibody (α-ghrelin Ab), (*$P<0.05$,**$P<0.01$ vs 0 μg/ml α-ghrelin Ab in each condition).

Together, these results show that unaclyated ghrelin counteracts apoptosis induced by serum starvation and IFN-γ/TNF-α combination in HIT-T15 cells. Moreover, they strongly indicate that even endogenous unacylated ghrelin exerts cytoprotective effects, likely via autocrine/paracrine mechanisms.

cAMP and its principal target, the cAMP-dependent PKA, play important roles in mammalian cell proliferation and apoptosis. Elevation of intracellular cAMP levels has been shown to promote cell growth and to delay apoptosis in different cell types, including pancreatic β-cells. Previous results showed that ghrelin-induced HIT-T15 cell proliferation involves the $G\alpha_s$ protein-coupled receptor, which, in turn, has been shown able to activate cAMP/PKA signaling; therefore, it was investigated whether the proliferative and antiapoptotic effects of unacylated ghrelin is mediated by this pathway.

Figure 10A:
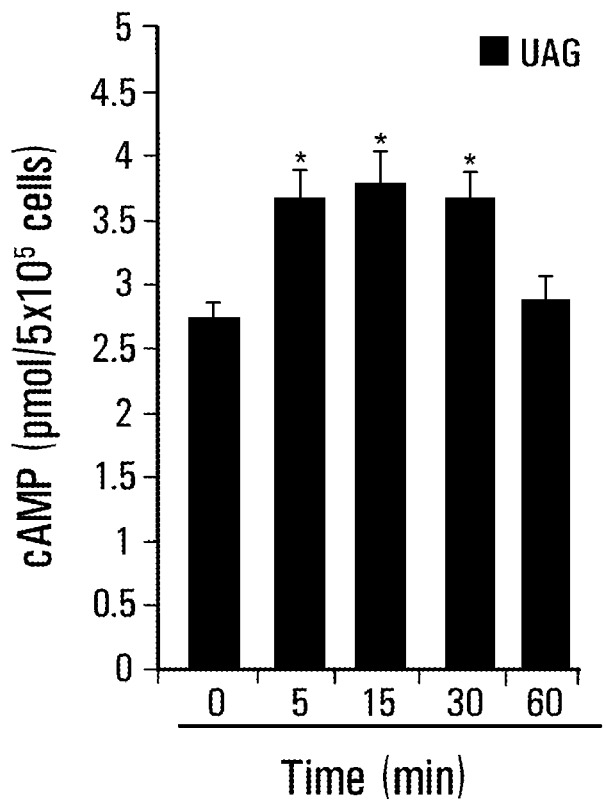
FIG. 10A illustrates the effect of unacylated ghrelin stimulation for the indicated time, of intracellular cAMP concentration in HIT-T15 cells.

Initially, the unacylated ghrelin-induced cAMP intracellular variation was examined. FIG. 10A shows that incubation of HIT-T15 cells with the unacylated ghrelin peptide, in the presence of the phosphodiesterase inhibitor IBMX, resulted in time-dependent changes of cAMP levels. Unacylated ghrelin produced a transient increase within 5 min, which was lower but still significantly above basal level at 10 and 30 min, declining thereafter toward the resting level after 60 min incubation.

cAMP induction by ghrelin was then evaluated at 15 min in either serum-free medium alone or with addition of IFN-γ/TNF-α in the presence of IBMX. Results showed that unacylated ghrelin significantly up-regulated cAMP not only in serum-free medium alone but also after incubation with cytokines that, per se, reduced cAMP levels (FIG. 10B).

Figure 10B:
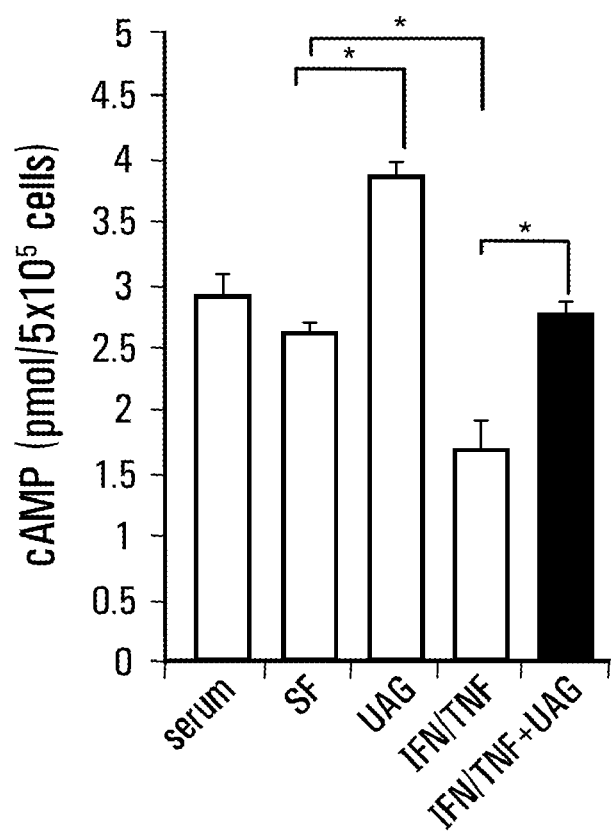
FIG. 10B illustrates the effect of unacylated ghrelin on cAMP levels in HIT-T15 cells incubated in the presence of serum or in serum-free (SF) medium±unacylated ghrelin alone or with IFN-γ/TNF-α combination.

FIGS. 10A and 10B demonstrate the effect of unacylated ghrelin on intracellular cAMP concentration in HIT-T15 cells. In FIG. 10A, serum starved cells were cultured for the indicated times with 100 nM of unacylated ghrelin. The results are the mean±SEM of three independent experiments performed in triplicate (*P<0.05 vs basal time point). FIG. 10B illustrates the cAMP levels in cells incubated in the presence of serum or in serum-free (SF) medium±unacylated ghrlein (100 nM each) alone or with IFN-γ/TNF-α combination (100 ng/ml and 200 ng/ml respectively). Data are the mean±SEM of at least three independent experiments performed in triplicate (*P<0.05).

In this invention, it is demonstrated that unacylated ghrelin has a glucose lowering effect since unacylated ghrelin prevents the hyperglycemic effects of acylated ghrelin. The results presented herein also indicate that unacylated ghrelin has an insulin sensitizing effect, reduces cortisol and growth hormone levels, and reduces glycemia. The results in healthy volunteers clearly showed that unacylated ghrelin alone is able to reduce blood glucose levels and improve insulin sensitivity.

The data presented herein also demonstrate that unacylated ghrelin decreases free fatty acids (FFA) in blood, indicating an effect of unacylated ghrelin on dyslipidemia. It might be expected that more prolonged treatments with unacylated ghrelin will have an effect on other lipids, such as, but not limited to triglycerides. In addition to these properties, unacylated ghrelin is capable of stimulating the proliferation and the survival as well as inhibiting death of insulin-secreting cells such as, but not limited to, pancreatic β cells.

In another aspect, the present invention provides for applications of unacylated ghrelin in the reduction, treatment and prevention of diseases, disorders and/or conditions associated with impaired glucose, insulin and lipid metabolism. The present invention also provides for an application of unacylated ghrelin and its analogs in modulating the proliferation of insulin-secreting cells. Such disorders and/or conditions include, but not limited to, type I diabetes, type II diabetes, the metabolic syndrome, dyslipidemia, and any medical conditions associated with insulin resistance. Unacylated ghrelin or its analogs can also be used to improve the quality of beta islets grafts prior to engraftment, and also improve the survival of beta cells in a patient following engraftment.

Hence, in this invention it was shown that unacylated ghrelin acts as an anti-diabetogenic agent with applications in the prevention and treatment of metabolic disorders associated with the metabolic syndrome, or syndrome X. Indeed, the demonstrated action of unacylated ghrelin to reduce blood glucose levels, to improve insulin sensitivity, to decrease blood free fatty acids (FFA) and cortisol levels, as well as its action to promote proliferation of insulin-secreting pancreatic β-cells are indicative of this anti-diabetogenic effect.

In accordance with a further aspect of the invention, therapeutic compositions of the present invention, comprising a therapeutically effective amount of an agent selected from the group consisting of an unacylated ghrelin, an analog thereof and a pharmaceutically acceptable salt thereof, may be provided in containers or commercial packages which further comprise instructions for use of a therapeutically effective amount of an agent selected from the group consisting of an unacylated ghrelin, an analog thereof and a pharmaceutically acceptable salt thereof for the prevention and/or treatment of diseases.

Accordingly, the invention further provides a commercial package comprising a therapeutically effective amount of an agent selected from the group consisting of an unacylated ghrelin, an analog thereof and a pharmaceutically acceptable salt thereof or the above-mentioned composition together with instructions for the prevention and/or treatment of diseases.

It is understood that the data reported in the present specification are only given to illustrate the invention and may not be regarded as constituting a limitation thereof.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A method for enhancing survival and/or proliferation of insulin-secreting cells comprising culturing said cells in the presence of a therapeutically effective amount of an agent selected from the group consisting of (a) unacylated ghrelin; (b) the unacylated ghrelin of (a) having one or more conservative amino acid substitutions; and (c) pharmaceutically acceptable salts of (a) or (b).

2. The method of claim 1, wherein unacylated ghrelin consists of the amino acid sequence set forth in SEQ ID NO: 1.

3. The method of claim 1, wherein the insulin-secreting cells are pancreatic β-cells.

4. The method of claim 1, wherein the cultured cells are suitable for engraftment.

5. A method for inhibiting death of insulin-secreting cells comprising culturing said cells in the presence of a therapeutically effective amount of an agent selected from the group consisting of (a) unacylated ghrelin; (b) the unacylated ghrelin of (a) having one or more conservative amino acid substitutions; and (c) pharmaceutically acceptable salts of (a) or (b).

6. The method of claim 5, wherein unacylated ghrelin consists of the amino acid sequence set forth in SEQ ID NO: 1.

7. The method of claim 5, wherein the insulin-secreting cells are pancreatic β-cells.

8. The method of claim 5, wherein the cultured cells are suitable for engraftment.

* * * * *

SEQUENCE LISTING

<160> NUMBER OF SEQ ID NOS: 1

<210> SEQ ID NO 1
<211> LENGTH: 28
<212> TYPE: PRT
<213> ORGANISM: Artificial sequence
<220> FEATURE:
<223> OTHER INFORMATION: synthetic polypeptide: unacylated ghrelin

<400> SEQUENCE: 1

Gly Ser Ser Phe Leu Ser Pro Glu His Gln Arg Val Gln Gln Arg Lys
1               5                   10                  15

```
Glu Ser Lys Lys Pro Pro Ala Lys Leu Gln Pro Arg
            20                  25
```